United States Patent [19]
Weyl et al.

[11] Patent Number: 6,083,371
[45] Date of Patent: Jul. 4, 2000

[54] SEALING DEVICE FOR GAS SENSOR

[75] Inventors: Helmut Weyl, Schwieberdingen; Udo Jauernig, Leonberg, both of Germany

[73] Assignee: Robert Bosch GmbH, Stuttgart, Germany

[21] Appl. No.: 08/930,347

[22] PCT Filed: Oct. 31, 1996

[86] PCT No.: PCT/DE96/02136

§ 371 Date: Sep. 30, 1997

§ 102(e) Date: Sep. 30, 1997

[87] PCT Pub. No.: WO97/28442

PCT Pub. Date: Aug. 7, 1997

[30] Foreign Application Priority Data

Jan. 31, 1996 [DE] Germany .......................... 196 03 379

[51] Int. Cl.[7] .................. G01N 27/416; G01N 27/407
[52] U.S. Cl. .................. 204/426; 204/424; 204/428; 277/943
[58] Field of Search .................. 204/421–429; 277/522, 531, 534, 541, 542, 943

[56] References Cited

U.S. PATENT DOCUMENTS

| 4,310,401 | 1/1982 | Stahl . |
| 4,818,363 | 4/1989 | Bayha et al. . |
| 5,302,274 | 4/1994 | Tomantschger et al. . |
| 5,467,636 | 11/1995 | Thompson et al. . |
| 5,846,391 | 12/1998 | Friese et al. . |

FOREIGN PATENT DOCUMENTS

| 0398579A | 11/1990 | European Pat. Off. . |
| 4126378A | 4/1992 | Germany . |

Primary Examiner—Robert J. Warden, Sr.
Assistant Examiner—Jennifer McNeil
Attorney, Agent, or Firm—Venable; George H. Spencer; Ashley J. Wells

[57] ABSTRACT

A gas sensor including a sealing arrangement for sensing exhaust gases of internal combustion engines includes a housing for the sealing arrangement having a longitudinal bore; a planar sensor element secured in the longitudinal bore of the housing; a spring element; upper and lower molded parts that are pressed together by means of the spring element; and a sealing material comprised of a ceramic powder and disposed between the upper and lower molded parts and surrounding the sensor element in a gas-tight manner, wherein the lower molded part consists of a disk-shaped base part and a ring that rests on the disk-shaped base part so that an inside space is defined within the ring for holding the ceramic powder, wherein the upper molded part has a ring-shaped, stepped recess which is pressed into the inside space of the lower molded part, and wherein the ceramic powder in the inside space is held in a compressed state due to compressing forces exerted by the spring element. In another embodiment, the gas sensor includes first and second molded parts that are pressed together by means of the spring element; and a sealing material disposed between the first and second molded parts and surrounding the sensor element in a gas tight manner, wherein the first molded part has a cylindrical segment and a conical segment which define an inside space with the planar sensor element, wherein the conical segment has a conically sloped surface, and wherein the sealing material is contained within the inside space, wherein the second molded part has a ring-shaped, stepped recess which is pressed into the inside space along the cylindrical segment, and wherein the conically sloped surface extends at a preselected angle ($\alpha$) to the longitudinal axis of the sensor element and at least one of degree of compression and plastic deformation of the sealing material is adjusted by varying the angle ($\alpha$).

8 Claims, 2 Drawing Sheets

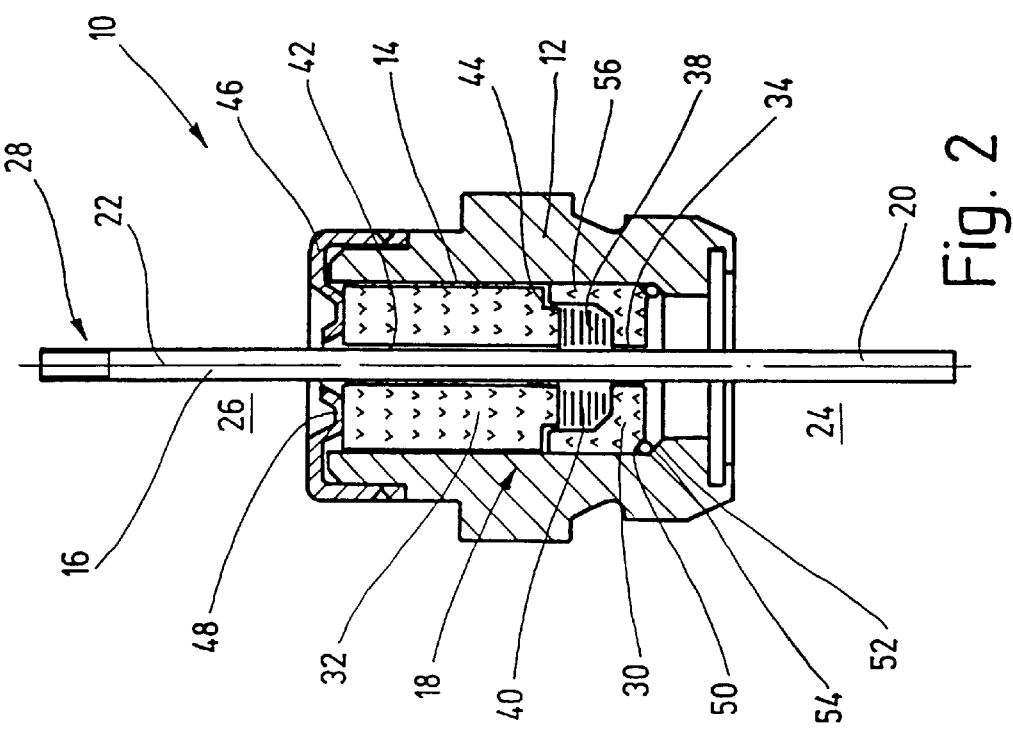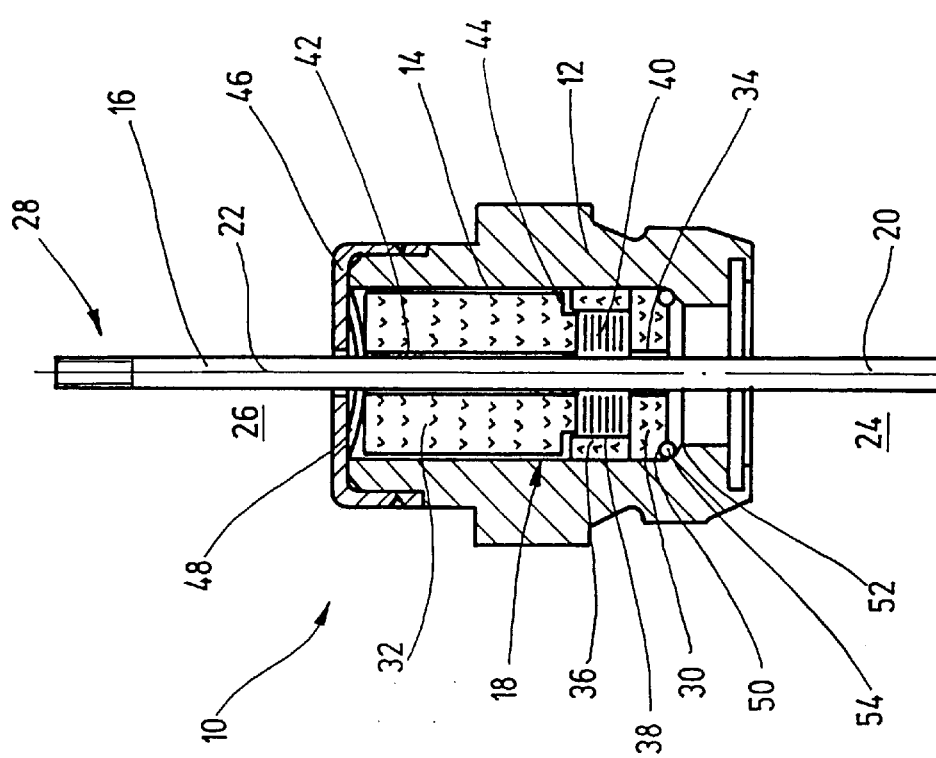

SEALING DEVICE FOR GAS SENSOR

BACKGROUND OF THE INVENTION

1. Field of the Invention

The invention relates to a gas sensor, particularly for exhaust gases of internal combustion engines, having a planar sensor element that is fixed in a longitudinal bore of a housing of a sealing arrangement that has two molded parts that can be pressed together by means of a spring element, and has a sealing material that is disposed between the molded parts and surrounds the sensor element.

2. Description of the Related Art

Gas sensors of the generic type are known. For example, DE 32 06 903 A1 discloses a gas sensor in which a planar sensor element is fixed in a longitudinal bore of a housing with two superposed, electrically-insulating molded parts. Between the molded parts, the sensor element is surrounded by an electrically-insulating powder that is compressed during assembly and is maintained in its compressed state by a spring element. Inside the housing, the powder forms a seal for the sensor element that separates a measured-gas chamber and a reference-gas chamber for the sensor element. It is known to use steatite as the sealing powder. A disadvantage of this is that, on the one hand, the steatite powder has a residual porosity that can cause leakages between the measured-gas chamber and the reference-gas chamber. Another disadvantage is that the steatite powder has a lower thermal expansion coefficient than the surrounding housing, so leakages can also occur due to heating of the gas sensor over the course of operation.

SUMMARY OF THE INVENTION

In contrast, in the gas sensor of the invention at least one of the molded parts forms a receptacle for the sealing material, and the spring element causes the sealing material to be compressed and/or plastically deformed into this receptacle by the further molded part, and the sealing material is maintained in the compressed and/or plastically-deformed position. This has the advantage of reliably maintaining a seal between the measured-gas chamber and the reference-gas chamber, even with extreme mechanical and/or thermal stress of the gas sensor. Because at least one of the molded parts of the sealing arrangement forms a receptacle for the sealing material, and a spring element causes the sealing material to be compressed and/or plastically deformed in this receptacle by the further molded part, and the sealing material is maintained in the compressed and/or plastically-deformed position, it is advantageously possible to exert a strong pressing force onto the sealing material such that the material is compressed enough to reliably preclude a connection between the measured-gas chamber and the reference-gas chamber, both by the sealing material itself and at the contact surfaces between the sealing material and the sensor element.

It is particularly advantageous if the molded parts that receive the sealing material have a lower thermal expansion coefficient than the sealing material. This advantageously permits the sealing material to expand more than the molded parts during operation-stipulated heating of the sensor element, and thus of the sealing material and the molded parts, so the sealing effect is at least retained, if not increased.

Further, advantageous embodiments of the invention ensue from its other features, which are disclosed in the dependent claims.

BRIEF DESCRIPTION OF THE DRAWINGS

The invention is described in detail below by way of embodiments illustrated in the attached drawings. Shown are in:

FIG. 1 a longitudinal section through a sealing arrangement of a gas sensor according to a first embodiment variation, FIG. 2 a longitudinal section through a sealing arrangement of a gas sensor according to a second embodiment variation, and FIG. 3 a partial longitudinal section through a sealing arrangement of a gas sensor according to a third embodiment variation.

DESCRIPTION OF THE EMBODIMENTS

Figure 3:
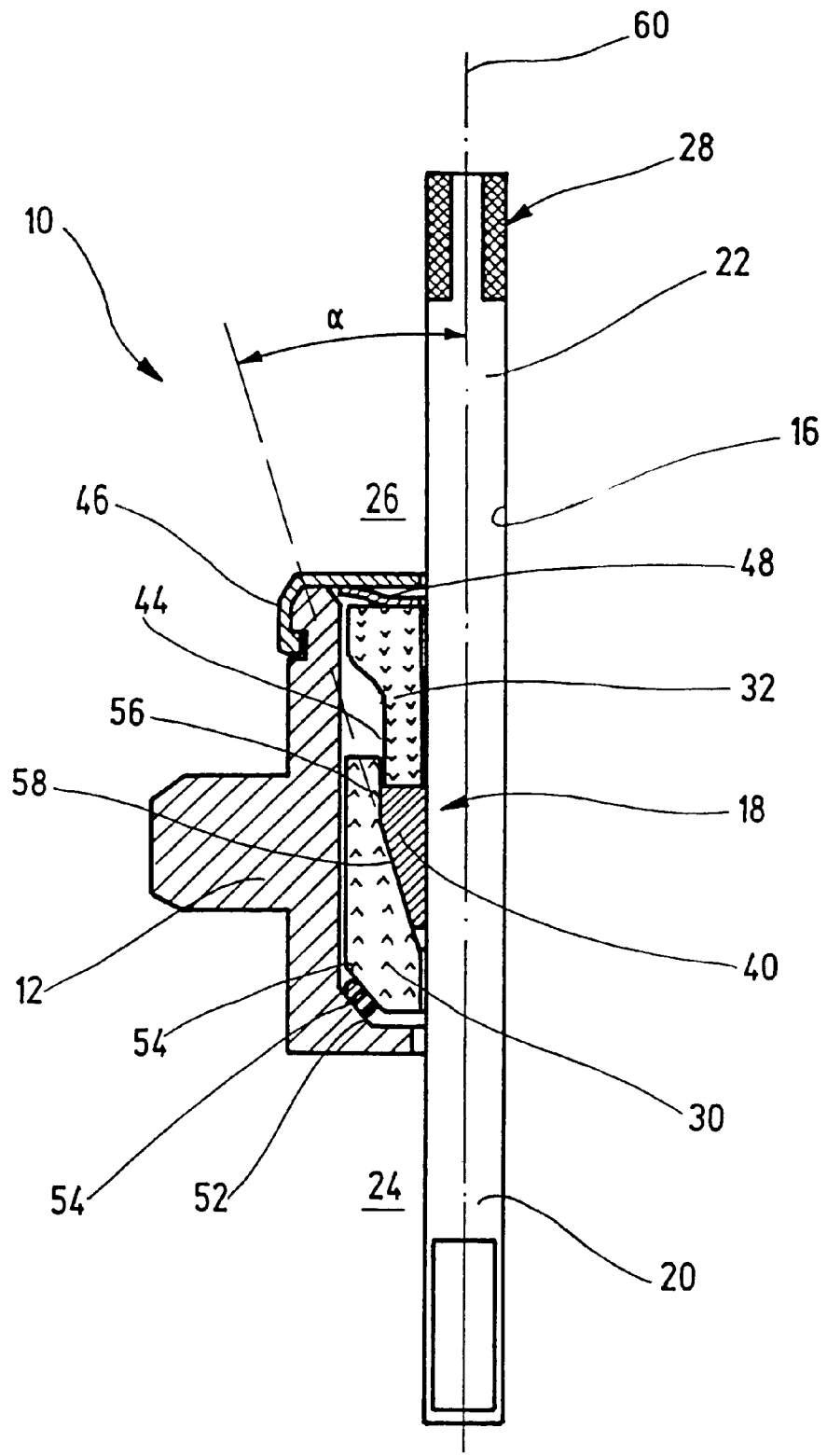

FIGS. 1 through 3 show sectional views of a gas sensor 10 with its components that are essential to the present invention. For better clarification, identical parts shown in the different figures are provided with the same reference numerals, despite their varying constructions.

FIG. 1 shows a gas sensor 10. The gas sensor 10 has a housing 12; a planar sensor element 16 is guided through a longitudinal bore 14 of the housing. The sensor element 16 is fixed in the housing 12 by a sealing arrangement 18. The sensor element 16 has a section 20 on the side of the measured gas, and a section 22 on the side of the reference gas. The section 20 on the side of the measured gas projects into a measured-gas chamber 24, while the section 22 on the side of the reference gas projects into a reference-gas chamber 26. The section 22 has contacts 28, not shown in detail here, for electrically contacting the sensor element 16. The sealing arrangement 18 seals the measured-gas chamber 24 from the reference-gas chamber 26, with the housing 12 being secured in, for example, the exhaust-gas pipe of a motor vehicle.

The sealing arrangement 18 has a molded part 30 on the side of the measured gas, and a molded part 32 on the side of the reference gas. The molded part 30 is essentially disk-shaped, and has a throughgoing opening 34 for the sensor element 16. A ring 36 whose outer circumference rests against the inside wall of the housing 12 is supported on the molded part 30; this ring forms an inner chamber 38. The inner chamber 38 is filled with a sealing material 40. The second molded part 32 is essentially cylindrical, and likewise has a throughgoing opening 42 for the sensor element 16. On its end face facing the ring 36, the molded part 32 has an annular, stepped recess 44. The stepped recess 44 and the ring 36 are configured such that they can be displaced one inside the other, with a snug fit, over a selectable length.

The housing 12 can be closed by means of a lid 46, which can be latched or screwed to the housing, for example, or secured to it in some other, suitable manner, or welded to it. The lid 46 has on its side facing the sealing arrangement 18 at least one spring element 48, for example a formed-on disk spring.

On its side facing the measured-gas chamber 24, the molded part 30 has a conical annular shoulder 50, which corresponds to an annular step 52 of the housing 12. A sealing ring 54 is inserted into the annular step 52.

The sealing material 40 comprises, for example, a material that can easily be plastically deformed, such as a metal or a ceramic powder (steatite, boron nitride). The molded parts 30 and 32 and the ring 36 comprise a high-strength, electrically-insulating material, so the sensor element 16 is fixed, with electrical insulation, with respect to the housing 12. The molded parts 30 and 32 and the ring 36 can comprise a high-strength ceramic, such as aluminum oxide $Al_2O_3$ or silicon nitride $Si_3N_4$. The material of the molded parts 30 and 32 and the ring 36 is matched to the sealing material 40 such that a thermal expansion coefficient of the sealing material 40 is larger than or identical to the thermal expansion coefficient of the molded parts 30, 32 and 36. Moreover, the material is selected such that a thermal expansion coefficient of the sensor element 16, which typically comprises zirconium oxide $ZrO_2$, is larger than the thermal expansion coefficient of the sealing material 40. A powdered boron nitride, for example, can be used as the sealing material 40.

In the assembly of the sensor element 16, the lid 46 is placed onto the housing 12; thus, a pressing force is exerted on the molded part 32 by way of the spring element 48. The molded part is displaced into the ring 36, along the stepped recess 44, and thereby compresses the sealing material 40. The pressing force occurring in the process suffices to plastically deform the sealing material 40. In addition to the compression, this effects an optimum adaptation of the sealing material 40 to the contours of the sensor element 16, the molded parts 30 and 32, respectively, and the ring 36. Thus, slight production tolerances and/or possibly present burs caused by production can be compensated. After the lid 46 has reached its end position, the joining forces are maintained by the spring element 48, so the sealing material 40 is permanently acted upon by a pressing force, also in the intended use of the gas sensor 10. Therefore, jarring or the like cannot result in a diminished sealing effect of the sealing arrangement 18. Due to the hardness of the material of the sensor element 16, the introduction of pressing forces into the sealing material 40 causes the sealing material 40 to conform very well to the sensor element 16, preventing any connection between the measured-gas chamber 24 and the reference-gas chamber 26. The plastic deformation of the sealing material 40 prevents leakages caused by possibly present residual porosity.

Through the selection of the thermal expansion coefficients of the materials of the sensor element 16, the sealing material 40 and the molded parts 30, 32 and 36, the molded parts 30, 32 and 36 experience less expansion than the sealing material 40 during operation-stipulated heating of the gas sensor 10, and the sealing material in turn experiences less expansion than the sensor element 16. Consequently, leakages occurring due to differing expansions of the individual materials are counteracted; in contrast, the selection of the thermal expansion coefficients reinforces the sealing effect during heating.

FIG. 2 shows the gas sensor 10 in a second embodiment variation. In contrast to FIG. 1, the molded part 30 and the ring 36 are embodied in one piece. The molded part 30 has a raised edge 56, which forms a trough-shaped inner chamber 38 for receiving the sealing material 40. The edge 56 of the molded part 30 and the stepped recess 44 of the molded part 32 form a snug fit.

The lid 46 of the embodiment shown in FIG. 2 possesses a shape that simultaneously ensures the formation of the spring element 48. The lid 46 possesses sufficient elasticity to effect a pressing force on the molded part 32 and thus on the sealing material 40 via the spring elements 48 when the lid is positioned on the housing 12.

The sealing ring 54 effects an additional seal between the molded part 30 and the housing 12.

In the embodiment shown in FIG. 3, the molded part 30 has a conically-sloped surface 58 for the sealing material 40.

The sloped surface 58 extends at an angle $\alpha$ with respect to an imaginary longitudinal axis 60 of the sensor element 16. Consequently, when the lid 46 is positioned, especially high pressing forces are exerted on the sealing material 40 via the spring element 48 and the molded part 32 that result in a severe compression or plastic deformation of the sealing material 40. The sealing material 40 is compressed into the narrowing gap between the sloped surface 58 of the molded part 30 and the sensor element 16, producing an optimum sealing effect. The pressing force acting on the sealing material 40 can be set through the selection of the angle $\alpha$. In the selection of a suitable, small angle $\alpha$, the sealing materials 40 are prevented from detaching by self-locking. The force acting on the sealing arrangement 18 by way of the spring element 48 serves solely to compensate settling processes occurring during the intended use of the gas sensor 10.

From the embodiments explained in conjunction with FIGS. 1 through 3, it becomes clear that a variation in the sealing arrangement 18, particularly a variation in the shape of the molded parts 30, 32 or 36, and a suitable selection of the molded parts material and the sealing material 40 achieve an improved sealing effect over known gas sensors 10. The basic design of the gas sensors 10 can be retained, because only the molded parts 30, 32 or 36 need to be correspondingly replaced.

What is claimed is:

1. Gas sensor including a sealing arrangement for sensing exhaust gases of internal combustion engines, comprising:

a housing for the sealing arrangement having a longitudinal bore;

a planar sensor element secured in the longitudinal bore of the housing;

a spring element;

first and second molded parts that are pressed together by means of the spring element, which spring element is positioned adjacent one of the upper molded part or the lower molded part; and a sealing material disposed between the first and second molded parts and surrounding the sensor element in a gas tight manner, wherein the first molded part has a cylindrical segment and a conical segment which define an inside space with the planar sensor element, wherein the conical segment has a conically sloped surface, and wherein the sealing material is contained within the inside space and in contact with the conical segment, wherein the second molded part has a ring-shaped, stepped recess which is pressed into the inside space along the cylindrical segment, and wherein the conically sloped surface extends at a preselected angle ($\alpha$) to the longitudinal axis of the sensor element and at least one of degree of compression and plastic deformation of the sealing material is adjusted by varying the angle ($\alpha$).

2. The gas sensor according to claim 1, wherein the sealing material has a higher thermal expansion coefficient than that of the upper and lower molded parts.

3. The gas sensor according to claim 1, wherein the sensor element has a higher thermal expansion coefficient than that of the sealing material.

4. The gas sensor according to claim 1, wherein the sealing material is a metal.

5. The gas sensor according to claim 1, wherein the sealing material is powdered boron nitride.

6. The gas sensor according to claim 1, wherein the upper and lower molded parts comprise a high-strength ceramic.

7. The gas sensor according to claim 6, wherein the high-strength ceramic is selected from the group consisting of aluminum oxide or silicon nitride.

8. The gas sensor according to claim 1, further comprising a lid which engages the spring element and is secured to the housing.

* * * * *